United States Patent [19]

Juniewicz et al.

[11] Patent Number: 5,175,155
[45] Date of Patent: Dec. 29, 1992

[54] WIN 49596-FINASTERIDE METHOD OF USE AND COMPOSITIONS

[75] Inventors: Paul E. Juniewicz, Clifton Park, N.Y.; Bruce M. Berger, Radnor Township, Delaware County, Pa.

[73] Assignee: Sterling Winthrop Inc., New York, N.Y.

[21] Appl. No.: 772,988

[22] Filed: Oct. 7, 1991

[51] Int. Cl.$^5$ .................. A61K 31/58; A61K 31/44
[52] U.S. Cl. .................................. 514/176; 514/284
[58] Field of Search ........................... 514/176, 284

[56] References Cited

U.S. PATENT DOCUMENTS 4,684,636 8/1987 Christiansen et al. ............. 514/176
4,760,071 7/1988 Rasmusson et al. ............... 514/284

OTHER PUBLICATIONS

USAN and the USP Dictionary of Drug Names, 1991, p. 257.
Labrie et al., Endocrinology, vol. 128, No. 3, pp. 1673-1675, 1991.

*Primary Examiner*—Jerome Goldberg
*Attorney, Agent, or Firm*—Theodore C. Miller; Paul E. Dupont; Imre Balogh

[57] ABSTRACT

The method of use of a combination of the antiandrogen (5α,17α)-1'-(methylsulfonyl)-1'H-pregn-20-yno[3,2-c]pyrazol-17-ol (Win 49596) and the 5α-reductase inhibitor (5α,17β)-N-(1,1-dimethylethyl)-3-oxo-4-azaandrost-1-ene-17-carboxamide (finasteride) for treating prostate disease in a male mammal and pharmaceutical compositions thereof are disclosed.

6 Claims, No Drawings

WIN 49596-FINASTERIDE METHOD OF USE AND COMPOSITIONS

BACKGROUND OF THE INVENTION

1. Field of the Invention

The invention relates to method of use of a combination of the antiandrogen (5α,17α)-1'-(methylsulfonyl)-1'H-pregn-20-yno[3,2-c]pyrazol-17-ol (Win 49596) and the 5α-reductase inhibitor (5α,17β)-N-(1,1-dimethylethyl)-3-oxo-4-azaandrost-1-ene-17-carboxamide (finasteride) for treating prostatic disease in a male mammal and pharmaceutical compositions thereof.

2. Information Disclosure Statement

Christiansen et al. U.S. Pat. No. 4,684,636 issued Aug. 4, 1987 describes antiandrogenic sulfonylsteroidopyrazoles including (5α,17α)-1'-(methylsulfonyl)-1'H-pregn-20-yno[3,2-c]pyrazol-17-ol as the product of EXAMPLE 1 and method of use thereof "for effecting an antiandrogenic response in a mammal" and as being "contemplated to be carried out in the human male in the treatment of benign prostatic hypertrophy" and pharmaceutical compositions thereof. The patent does not describe the combination of any sulfonylsteroidopyrazole thereof with any 5α-reductase inhibitor. (5α,17α)-1'-(methylsulfonyl)-1'H-pregn-20-yno[3,2-c]pyrazol-17-ol has been described by several publications in the pharmaceutical literature as Win 49596. The generic name zanoterone was recently approved by the United States Adopted Name Council for (5α,17α)-1'-(methylsulfonyl)-1'H-pregn-20-yno[3,2-c]pyrazol-17-ol.

Rassmusson et al. U.S. Pat. No. 4,760,071 issued Jul. 26, 1988 describes "17β-N-monosubstituted carbamoyl-4-aza-5α-androst-1-en-3-one compounds and the use of such compounds as testosterone-5α-reductase inhibitors" including as EXAMPLE 1a N-tert-butyl-3-oxo-4-aza-5α-androst-1-ene-17β-carboxamide and method of use thereof for "treating the hyperandrogenic condition[s] of acne vulgaris, seborrhea, femal[e] hirsutism, and benign prostatic hypertrophy" and pharmaceutical compositions "comprising a pharmaceutical carrier and an effective amount" thereof. The patent does not describe the combination of any 17β-N-monosubstituted carbamoyl-4-aza-5α-androst-1-en-3-one thereof with any antiandrogen.

USAN and the USP Dictionary of Drug Names (1991, p. 257) describes N-tert-butyl-3-oxo-4-aza-5α-androst-1-ene-17β-carboxamide by the Chemical Abstracts name (5α,17β)-N-(1,1-dimethylethyl)-3-oxo-4-azaandrost-1-ene-17-carboxamide and by the generic name finasteride and "[a]ntineoplastic; inhibitor (5 alpha reductase)" utility thereof.

Labrie et al. (Endocrinology, vol. 128, no. 3, pp. 1673–1675, 1991) describes the combination of the nonsteroidal antiandrogen flutamide with the 5α-reductase inhibitor 4-MA (17β,N,N-diethylcarbamoyl-4-methyl-4-aza-5α-androstan-3-one) and states that the inhibitory effects thereof "are additive on prostatic growth and on androgensensitive prostatic binding protein mRNA levels in the rat, thus clearly suggesting that such a combination could provide the basis for a further improvement in the therapy of prostate cancer."

The presently described and claimed invention provides a method of use and pharmaceutical compositions of the combination of Win 49596 and finasteride for reducing the size or inhibiting the growth of the prostate in a male mammal in less time than possible with either drug alone.

SUMMARY OF THE INVENTION

In a process aspect the invention is the method of reducing the size or inhibiting the growth of the prostate in a male mammal which comprises administering to the mammal an effective amount of a combination of (5α,17α)-1'-(methylsulfonyl)-1'H-pregn-20-yno[3,2-c]pyrazol-17-ol and (5α,17β)-N-(1,1-dimethylethyl)-3-oxo-4-azaandrost-1-ene-17-carboxamide.

In a composition of matter aspect the invention is a pharmaceutical composition for reducing the size or inhibiting the growth of the prostate in a male mammal which comprises an effective concentration of a combination of (5α,17α)-1'-(methylsulfonyl)-1'-H-pregn-20-yno[3,2-c]pyrazol-17-ol and (5α,17β)-N-(1,1-dimethylethyl)-3-oxo-4-azaandrost-1-ene-17-carboxamide in a pharmaceutical vehicle.

DETAILED DESCRIPTION OF THE INVENTION INCLUSIVE OF THE PREFERRED EMBODIMENTS

The combination of (5α,17α)-1'-(methylsulfonyl)-1'H-pregn-20-yno[3,2-c]pyrazol-17-ol (Win 49596) and (5α,17β)-N-(1,1-dimethylethyl)-3-oxo-4-azaandrost-1-ene-17-carboxamide (finasteride) of the invention is effective in reducing the size or inhibiting the growth of the prostate in a male mammal and is therefore indicated for treatment of benign hyperplastic or hypertrophic growth or malignant neoplastic or cancerous growth of the prostate in a male mammal including a human.

The method of use aspect of the invention can be carried out in any male mammal including a human in need of reduction of size or inhibition of growth of the prostate including a benign hyperplastic or benign hypertrophic or malignant neoplastic or cancerous prostate and has been demonstrated in the dog.

Adult male purebred beagle dogs having a mean age of 34±18 (standard deviation) months and each having an ultrasound-estimated prostate weight of at least 10 grams were used. Four dogs were assigned to each of the following ten treatment groups: intact controls, castrate controls, 2.5 mg/kg of Win 49596 alone, 10 mg/kg of Win 49596 alone, 0.25 mg/kg of finasteride alone, 1.0 mg/kg of finasteride alone, 2.5 mg/kg of Win 49596 plus 0.25 mg/kg of finasteride, 2.5 mg/kg of Win 49596 plus 1.0 mg/kg of finasteride, 10 mg/kg of Win 49596 plus 0.25 mg/kg of finasteride, 10 mg/kg of Win 49596 plus 1.0 mg/kg of finasteride. Crystalline drugs and drug mixtures in these amounts were encapsulated in hard gelatin capsules for oral administration. Empty capsules were administered to intact controls and castrate controls. Each dog received one capsule of its assigned dosage each day for 16 weeks. The dogs were fed after each dosing.

Prostate sizes were determined by transrectal ultrasonography during the two weeks prior to the beginning of medication and at 1,2,4,8,12 and 16 weeks after the beginning of medication. Day 1 for castrate controls was set as the day following castration. Prostate weights were calculated from thus determined prostate sizes by the method of Juniewicz et al. (Prostate, vol. 14, pp. 55–64, 1989). The results shown in Table I were obtained.

TABLE I

| Treatment Group | Ultrasound Prostate Weights Week of Treatment/Mean Weight (Grams ± Standard Error, n = 4) | | | | | | |
|---|---|---|---|---|---|---|---|
| | Pre | 1 | 2 | 4 | 8 | 12 | 16 |
| Intact Controls | 15.0 ± 2.3 | 15.4 ± 3.2 | 14.4 ± 2.1 | 18.1 ± 4.0 | 16.9 ± 3.6 | 16.9 ± 4.4 | 18.2 ± 3.3 |
| Castrate Controls | 16.2 ± 2.0 | 7.3 ± 0.3 | 6.4 ± 0.7 | 4.9 ± 0.4 | 5.0 ± 0.5 | 4.0 ± 0.4 | 4.5 ± 0.2 |
| Win 49596 (2.5 mg) | 15.8 ± 1.7 | 13.2 ± 1.2 | 13.4 ± 0.6 | 14.6 ± 0.7 | 13.6 ± 0.2 | 14.8 ± 0.9 | 12.9 ± 0.7 |
| Win 49596 (10 mg) | 17.2 ± 3.1 | 14.2 ± 1.9 | 13.2 ± 1.7 | 13.1 ± 2.2 | 10.8 ± 2.5 | 10.4 ± 1.9 | 11.1 ± 1.9 |
| Finasteride (0.25 mg) | 16.8 ± 3.2 | 11.7 ± 2.4 | 10.8 ± 2.7 | 8.4 ± 2.2 | 7.2 ± 2.0 | 7.1 ± 1.8 | 6.5 ± 1.1 |
| Finasteride (1.0 mg) | 16.1 ± 2.6 | 11.8 ± 2.0 | 12.6 ± 0.4 | 10.1 ± 0.6 | 7.3 ± 0.6 | 6.0 ± 0.7 | 5.9 ± 0.6 |
| Win 49596-Finasteride (2.5 mg-0.25 mg) | 15.9 ± 2.5 | 13.1 ± 2.3 | 10.5 ± 0.8 | 8.2 ± 0.6 | 7.2 ± 0.8 | 6.7 ± 1.2 | 6.6 ± 1.0 |
| Win 49596-Finasteride (2.5 mg-1.0 mg) | 15.3 ± 2.3 | 11.3 ± 2.4 | 8.6 ± 1.2 | 7.6 ± 1.3 | 6.2 ± 1.5 | 6.4 ± 2.2 | 6.7 ± 1.6 |
| Win 49596-Finasteride (10 mg-0.25 mg) | 15.2 ± 2.4 | 10.2 ± 0.7 | 7.4 ± 0.1 | 6.7 ± 0.2 | 5.2 ± 0.5 | 5.3 ± 0.5 | 5.2 ± 0.3 |
| Win 49596-Finasteride (10 mg-1.0 mg) | 15.0 ± 2.0 | 8.8 ± 1.4 | 8.7 ± 1.1 | 6.1 ± 0.8 | 4.9 ± 0.9 | 4.2 ± 0.5 | 4.4 ± 0.5 |

The time to 50% reduction in prostate weight and the time to 70% reduction in prostate weight were calculated for each dog and analyzed using survival analysis techniques. Survival distributions (distributions of times to prostatic weight reductions) for each treatment group were estimated using the product limit method of Kaplan and Meier (Journal of the American Statistical Association, vol. 53, pp. 457–781, 1958). Equality of survival distributions among treatment groups was compared using log rank and Wilcoxon test statistics (Kalbfleish and Prentice, The Statistical Analysis of Failure Time Data, John Wiley and Sons, New York, 1980). If an overall treatment difference existed, the following eight treatment group comparisons were made:

- 2.5 mg/kg Win 49596 with 2.5 mg/kg-0.25 mg/kg Win 49596-finasteride
- 2.5 mg/kg Win 49596 with 2.5 mg/kg-1.0 mg/kg Win 49596-finasteride
- 10 mg/kg Win 49596 with 10 mg/kg-0.25 mg/kg Win 49596-finasteride
- 10 mg/kg Win 49596 with 10 mg/kg-1.0 mg/kg Win 49596-finasteride
- 0.25 mg/kg finasteride with 2.5 mg/kg-0.25 mg/kg Win 49596-finasteride
- 0.25 mg/kg finasteride with 10 mg/kg-0.25 mg/kg Win 49596-finasteride
- 1.0 mg/kg finasteride with 2.5 mg/kg-1.0 mg/kg Win 49596-finasteride
- 1.0 mg/kg finasteride with 10 mg/kg-1.0 mg/kg Win 49596-finasteride P-values were calculated. A comparision whose p-value is 0.05 or less is considered to be statistically significant.

Table II presents the median time to 50% reduction in prostate weight for each treatment group.

TABLE II

| Time to 50% Reduction in Ultrasound Prostate Weight | |
|---|---|
| Treatment Group | Median Time to 50% Reduction (Weeks) |
| Intact Controls | >16.0 |
| Castrate Controls | 1.2 |
| Win 49596 (2.5 mg/kg) | >16.0 |
| Win 49596 (10 mg/kg) | 13.7 |
| Finasteride (0.25 mg/kg) | 3.7 |
| Finasteride (1.0 mg/kg) | 8.0 |
| Win 49596-Finasteride (2.5 mg/kg-0.25 mg/kg) | 6.3 |
| Win 49596-Finasteride (2.5 mg/kg-1.0 mg/kg) | 3.6 |
| Win 49596-Finasteride (10 mg/kg-0.25 mg/kg) | 2.7 |
| Win 49596-Finasteride (10 mg/kg-1.0 mg/kg) | 2.9 |

Table III presents the results of the statistical analysis of the above-shown comparisons of times to 50% reduction in prostate weight.

TABLE III

| Statistical Analysis of Times to 50% Reduction in Ultrasound Prostate Weight | | |
|---|---|---|
| Comparison | Median Time to 50% Reduction (Weeks) | P-value |
| 2.5 mg/kg Win 49596 with | >16.0 | 0.04 |
| 2.5 mg/kg-0.25 mg/kg Win 49596-Finasteride | 6.3 | |
| 2.5 mg/kg Win 49596 with | >16.0 | 0.01 |
| 2.5 mg/kg-1.0 mg/kg Win 49596-Finasteride | 3.6 | |
| 10 mg/kg Win 49596 with | 13.7 | 0.03 |
| 10 mg/kg-0.25 mg/kg Win 49596-Finasteride | 2.7 | |
| 10 mg/kg Win 49596 with | 13.7 | 0.01 |
| 10 mg/kg-1.0 mg/kg Win 49596-Finasteride | 2.9 | |
| 0.25 mg/kg Finasteride with | 3.7 | 0.27 |
| 2.5 mg/kg-0.25 mg/kg Win 49596-Finasteride | 6.3 | |
| 0.25 mg/kg Finasteride with | 3.7 | 0.40 |
| 10 mg/kg-0.25 mg/kg Win 49596-Finasteride | 2.7 | |
| 1.0 mg/kg Finasteride with | 8.0 | 0.13 |
| 2.5 mg/kg-1.0 mg/kg Win 49596-Finasteride | 3.6 | |
| 1.0 mg/kg Finasteride with | 8.0 | 0.03 |

TABLE III-continued

| Statistical Analysis of Times to 50% Reduction in Ultrasound Prostate Weight | | |
|---|---|---|
| Comparison | Median Time to 50% Reduction (Weeks) | P-value |
| 10 mg/kg-1.0 mg/kg Win 49596-Finasteride | 2.9 | |

The differences between the time to 50% reduction in prostate weight of the 0.25 mg/kg finasteride treatment group and the times to 50% reduction in prostate weight of the 2.5 mg/kg-0.25 mg/kg Win 49596-finasteride and 10 mg/kg-0.25 mg/kg Win 49596-finasteride treatment groups are not statistically significant. Although the difference is not statistically significant, the time to 50% reduction in prostate weight of the 2.5 mg/kg-1.0 mg/kg Win 49596-finasteride treatment group is less than the time to 50% reduction in prostate weight of the 1.0 mg/kg finasteride treatment group. Otherwise the compared times to 50% reduction in prostate weight of the combination of Win 49596 and finasteride are significantly less than the times to 50% reduction in prostate weight of either drug alone and provide evidence that the combination of drugs is more effective for reducing the size or inhibiting the growth of the prostate in a male mammal in less time than either drug alone.

Table IV presents the median time to 70% reduction in prostate weight for each treatment group.

TABLE IV

| Time to 70% Reduction in Ultrasound Prostate Weight | |
|---|---|
| Treatment Group | Median Time to 70% Reduction (Weeks) |
| Intact Controls | >16.0 |
| Castrate Controls | 9.6 |
| Win 49596 (2.5 mg) | >16.0 |
| Win 49596 (10 mg) | >16.0 |
| Finasteride (0.25 mg) | >16.0 |
| Finasteride (1.0 mg) | >16.0 |
| Win 49596-Finasteride (2.5 mg/kg-0.25 mg/kg) | >16.0 |
| Win 49596-Finasteride (2.5 mg/kg-1.0 mg/kg) | >16.0 |
| Win 49596-Finasteride (10 mg/kg-0.25 mg/kg) | 11.9 |
| Win 49596-Finasteride (10 mg/kg-1.0 mg/kg) | 9.3 |

Table V presents the results of the statistical analysis of the above-shown comparisons of times to 70% reduction in prostate weight.

TABLE V

| Statistical Analysis of Times to 70% Reduction in Ultrasound Prostate Weight | | |
|---|---|---|
| Comparison | Median Time to 70% Reduction (Weeks) | P-value |
| 2.5 mg/kg Win 49596 with | >16.0 | 0.32 |
| 2.5 mg/kg-0.25 mg/kg Win 49596-Finasteride | >16.0 | |
| 2.5 mg/kg Win 49596 with | >16.0 | 0.32 |
| 2.5 mg/kg-1.0 mg/kg Win 49596-Finasteride | >16.0 | |
| 10 mg/kg Win 49596 with | >16.0 | 0.38 |
| 10 mg/kg-0.25 mg/kg Win 49596-Finasteride | 11.9 | |
| 10 mg/kg Win 49596 with | >16.0 | 0.08 |
| 10 mg/kg-1.0 mg/kg Win 49596-Finasteride | 9.3 | |
| 0.25 mg/kg Finasteride with | >16.0 | 0.92 |
| 2.5 mg/kg-0.25 mg/kg Win 49596-Finasteride | >16.0 | |
| 0.25 mg/kg Finasteride with | >16.0 | 0.38 |
| 10 mg/kg-0.25 mg/kg Win 49596-Finasteride | 11.9 | |
| 1.0 mg/kg Finasteride with | >16.0 | 0.92 |
| 2.5 mg/kg-1.0 mg/kg Win 49596-Finasteride | >16.0 | |
| 1.0 mg/kg Finasteride with | >16.0 | 0.05 |
| 10 mg/kg-1.0 mg/kg Win 49596-Finasteride | 9.3 | |

The difference between the time to 70% reduction in prostate weight of the 10 mg/kg-1.0 mg/kg Win 49596-finasteride treatment group and the time to 70% reduction in prostate weight of the 1.0 mg/kg finasteride treatment group is statistically significant. Although the differences are not statistically significant, the time to 70% reduction in prostate weight of the 10 mg/kg-1.0 mg/kg Win 49596-finasteride treatment group is also less than the time to 70% reduction in prostate weight of the 10 mg/kg Win 49596 treatment group, and the time to 70% reduction in prostate weight of the 10 mg/kg-0.25 mg/kg Win 49596-finasteride treatment group is less than the time to 70% reduction in prostate weight of the 10 mg/kg Win 49596 treatment group and the 0.25 mg/kg finasteride treatment group. Accordingly the times to 70% reduction in prostate weight also provide evidence that the combination of drugs is more effective for reducing the size or inhibiting the growth of the prostate in a male mammal in less time than either drug alone.

To carry out the method of use aspect of the invention in a human effective amounts of Win 49596 and finasteride in a combination thereof can be a Win 49596-finasteride weight ratio in the range from 1000:1 to 1:1, more preferably in the range from 100:1 to 1:1, and, as shown by the results of the above-described experiment in the dog, most preferably in the range from 50:1 to 5:1.

The compositions of the invention can be prepared for oral, parenteral or rectal administration and can be in solid or liquid dosage form including capsules, tablets, suppositories, solutions, suspensions and emulsions. Conventional pharmaceutically acceptable vehicles and techniques are used in preparing these dosage forms. A solid oral dosage form is preferred, most preferably a capsule. The capsule can be as simple as a hard or soft gelatin capsule filled with a mixture of the two drugs without any additional ingredient as described above but is preferably a hard or soft gelatin capsule filled with a mixture of the two drugs and a suitable diluent, most preferably a mixture of the two drugs coated onto sugar/starch beads with a polymer mixture, for example hydroxypropylmethyl cellulose, a polyethylene glycol and a polyoxyethylene-polyoxypropylene-polyoxyethylene block copolymer, in sufficient amount to provide the desired dosage of each drug in the capsule.

We claim:

1. The method of reducing the size or inhibiting the growth of the prostate in a male mammal which comprises administering to the mammal a combination of (5α, 17α)-1'-(methylsulfonyl)-1'H-pregn-20-yno[3,2-c]pyrazol17-ol and (5α,17β)-N-(1,1-dimethylethyl)-3-oxo-4-azaandrost-1-ene-17-carboxamide in a weight ratio in the range from 100:1 to 1:1.

2. The method according to claim 1 wherein the weight ratio of (5α,17α)-1'-(methylsulfonyl)-1'H-pregn-20-yno[3,2-c]pyrazol-17-ol and (5α,17β)-N-(1,1-dimethylethyl)-3-oxo-4-azaandrost-1-ene-17-carboxamide is in the range from 50:1 to 5:1.

3. A pharmaceutical composition which comprises a combination of (5α,17α)-1'-(methylsulfonyl)-1'H-pregn-20-yno[3,2-c]pyrazol-17-ol and (5α,17β)-N-(1,1-dimethylethyl)-3-oxo-4-azaandrost-1-ene-17-carboxamide in a weight ratio in the range from 100:1 to 1:1 in a pharmaceutical vehicle.

4. A pharmaceutical composition according to claim 3 wherein the weight ratio of (5α,17α)-1'-(methylsulfonyl)-1'H-pregn-20-yno[3,2-c]pyrazol-17-ol and (5α,17β)-N-(1,1-dimethylethyl)-3-oxo-4-azaandrost-1-ene-17-carboxamide in the composition is in the range from 50:1 to 1:1.

5. The method of reducing the size or inhibiting the growth of the prostate in a male mammal which comprises administering to the mammal an effective amount of a composition according to claim 3.

6. The method of reducing the size or inhibiting the growth of the prostate in a male mammal which comprises administering to the mammal an effective amount of a composition according to claim 4.

* * * * *